United States Patent [19]

Yoshida et al.

[11] Patent Number: 4,840,807
[45] Date of Patent: Jun. 20, 1989

[54] BRANCHED DEXTRIN PRODUCTION AND COMPOSITIONS CONTAINING SAME

[75] Inventors: Tsukasa Yoshida; Yoshio Ishige, both of Yotsukaido; Masaki Matsudaira; Tadashi Takahashi, both of Chiba, all of Japan

[73] Assignee: Sanmatsu Kōgyo Kabushiki Kaisha, Tokyo, Japan

[21] Appl. No.: 88,281

[22] Filed: Aug. 24, 1987

[51] Int. Cl.$^4$ ............................................. A23L 1/00
[52] U.S. Cl. ........................................ 426/48; 127/40; 127/46.2; 210/660; 426/656; 435/99; 536/46
[58] Field of Search .................... 127/38, 40, 46.2, 55, 127/36; 210/656, 660, 661, 662, 635, 198.2; 435/103, 99, 95; 536/46, 47, 51, 45; 426/658, 48

[56] References Cited

U.S. PATENT DOCUMENTS

| | | | |
|---|---|---|---|
| 2,983,613 | 5/1961 | Bohn | 426/658 |
| 3,002,823 | 10/1961 | Hodin | 210/635 |
| 3,663,369 | 5/1972 | Morehouse | 435/99 |
| 3,817,787 | 6/1974 | von Hertzen | 127/46.2 |
| 3,974,032 | 8/1976 | Harjes | 426/658 |
| 3,974,033 | 8/1976 | Harjes | 426/658 |
| 3,974,034 | 8/1976 | Horn | 426/658 |
| 4,042,714 | 8/1977 | Torres | 426/658 |
| 4,267,054 | 7/1981 | Yoritomi et al. | |
| 4,279,931 | 7/1981 | Verwaerde | 426/658 |
| 4,379,751 | 4/1983 | Youtomi | 210/659 |
| 4,447,532 | 5/1984 | Cober | 435/99 |
| 4,614,548 | 9/1986 | Cameron | 210/656 |

FOREIGN PATENT DOCUMENTS 205494 9/1986 Japan ................................ 435/99

Primary Examiner—Donald E. Czaja
Assistant Examiner—Carolyn Paden
Attorney, Agent, or Firm—Nixon & Vanderhye

[57] ABSTRACT

Branched dextrin and linear oligosaccharides are produced by degrading starch with alpha-amylase followed by fractionating with a gel-type filtering agent. The branched dextrin is useful in the food fabrication.

6 Claims, 1 Drawing Sheet

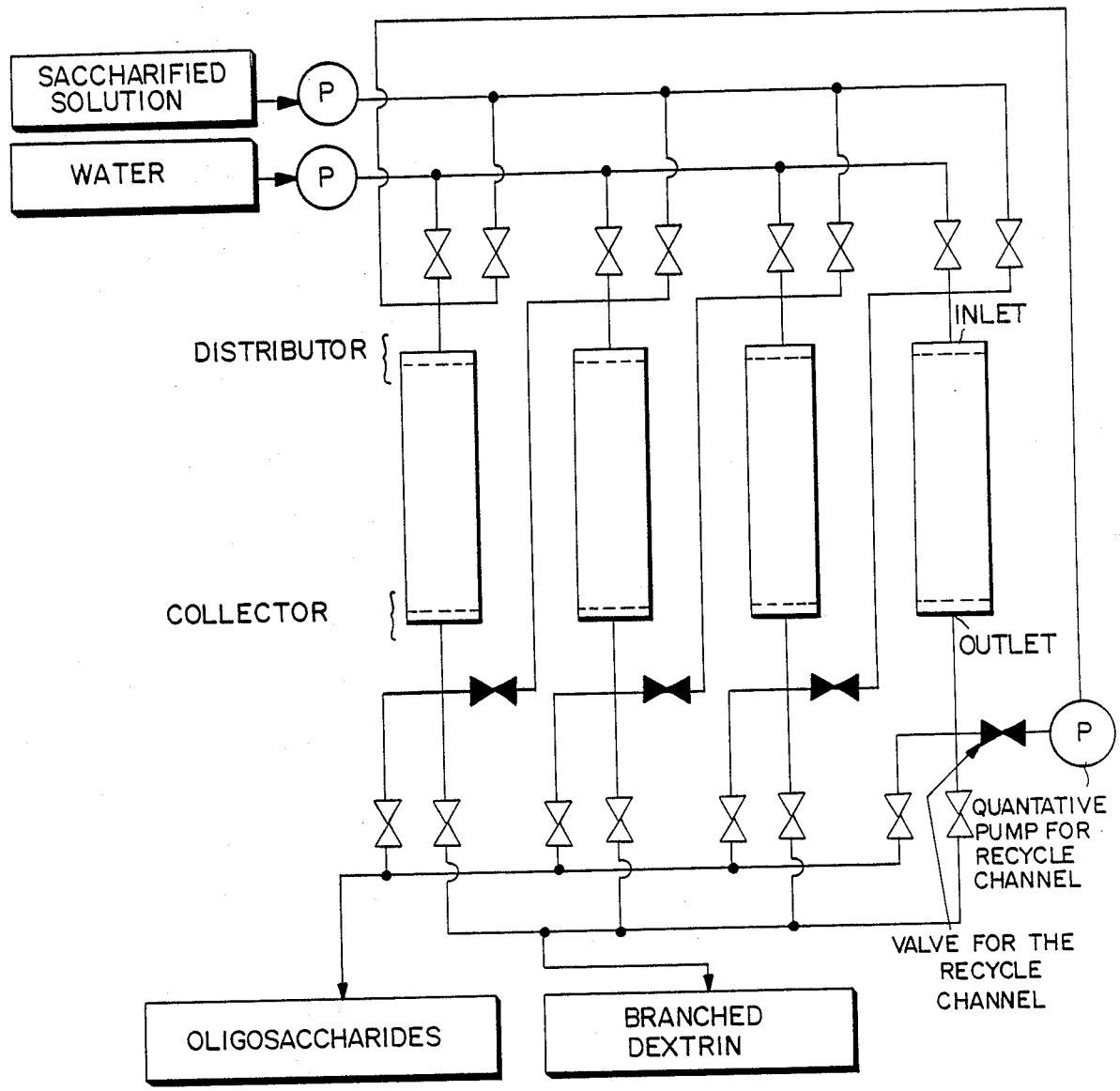

BRANCHED DEXTRIN PRODUCTION AND COMPOSITIONS CONTAINING SAME

BACKGROUND AND SUMMARY OF THE INVENTION

The present invention relates to a process for selectively fractionating branched dextrin and linear oligosaccharides from a starch-saccharified solution and utilizing the specific properties of the branched dextrin in food products.

Formerly, a process was established for fractionally producing maltose of a high purity and beta-limit dextrin (branched dextrin), which comprises the steps of reacting beta-amylase with liquefied starch, thereby forming a saccharified solution consisting mainly of maltose and beta-limit dextrin, and then contacting the thus saccharified solution with an OH-type anion exchange resin; see Japanese Patent Publication (KOKOKU) No. 46290/1977.

Maltose is a disaccharide formed by the alpha-1,4-linkage of two molecules of D-glucose and since maltose is lower in sweetness as compared to sucrose and D-glucose, it is broadly utilized as a sweetness-decreasing agent in the field of food fabrication. On the other hand, beta-limit dextrin is a macromolecule having a branched molecular structure and is referred to as branched dextrin. Due to its molecular structure, beta-limit dextrin is easily soluble into water in spite of being a macromolecule, it has a high viscosity, is stable and is not retrograded. Accordingly, beta-limit dextrin has attracted attention as a raw material for fabricating food products because it imparts elasticity to food products and is good in preserving moisture in the food products, i.e., is a humectant.

However, there is a recent demand for a material lower in sweetness than maltose and concerning branched dextrin, the physical properties of a material which has a lower molecular weight than beta-limit dextrin, have been requested by food processors and others.

Starch consists of both linear-structural amylose formed by polymerization of D-glucose through alpha-1,4-linkages and branched-structural amylopectin of which the main body is polymerized through alpha-1,4-linkages and the remaining moiety is branched through the alpha-1,6-linkage at various places of the main body.

In the case where beta-amylase is reacted with a liquefied solution of starch having the structure noted above, since only the linear-structural amylose and the outer branches of the branched-structural amylopectin become the target of the attack of beta-amylase and the internal structure is not destroyed, maltose and macromolecular branched dextrin are obtained. See Japanese Patent Publication (KOKOKU) No. 46290/1977. However, in the case where alpha-amylase is reacted with starch, not only amylose but also the alpha-1,4-linkages of the internal structure of amylopectin are cleaved randomly and the alpha-1,6-linkages are not attacked. Accordingly, as a result, a saccharified solution of the linear oligosaccharides which are higher in degree of polymerization than maltose and branched dextrin which is lower in molecular weight than beta-limit dextrin are obtained.

As a result of the present inventors' studies, the inventors have noticed the above-mentioned facts, from the viewpoint that if a process of selectively fractionating the linear oligosaccharides which are higher in degree of polymerization than maltose and the branched dextrin which is lower in molecular weight than beta-limit dextrin from a saccharified solution of starch (which solution comprises the linear oligosaccharides and the branched dextrin) can be offered in order to simultaneously satisfy the above-mentioned recent demands in the market, it is possible to answer these recent market demands and, accordingly, the range of application of such linear oligosaccharides and branched dextrin to food products would be remarkably enlarged.

In Japanese Patent Publication (KOKOKU) No. 46290/1977 noted above, maltose and macromolecular beta-limit dextrin can be separated effectively from a saccharified solution of maltose and beta-limit dextrin utilizing the adsorptive property of maltose to an OH-type anion exchange resin. However, a saccharified solution resulting from the degradation of starch with alpha-amylase containing branched dextrin and linear oligosaccharides, it has been found that there is no difference between the absorptive properties of the linear oligosaccharides and that of the branched dextrin to an OH-type anion exchange resin. This means that the two substances cannot be effectively separated with an OH-type anion exchange resin.

Thus, it is a problem to fractionate the above-mentioned branched dextrin and linear oligosaccharides respectively from the saccharified solution containing the two.

As a result of the present inventors' studies fractionating branched dextrin and linear oligosaccharides from a degradation product of starch by alpha-amylase, the inventors have found that differences are caused between the internal invasions to a gel-filtrating agent or between the sliding speeds on the surface, depending upon the difference between the linear molecular structure of the oligosaccharides and the branched molecular structure of the dextrin in the degradation product of starch. Utilizing these differences, the present inventors have succeeded in effectively fractionating the branched dextrin and linear oligosaccharides respectively from a saccharified solution of the degradation product of starch.

Accordingly, an object of the present invention is to provide a process for effectively and selectively fractionating branched dextrin and linear oligosaccharides from a saccharified solution which has been obtained by applying alpha-amylase to starch and consists mainly of the branched dextrin and the linear oligosaccharides, and at the same time, in offering a method for utilizing the thus fractionated products for food products based on the physical properties of the resulting fractionated products.

The present invention will be explained in detail as follows.

BRIEF DESCRIPTION OF THE DRAWING

FIG. 1 is a schematic illustration of a separation appratus for carrying out the process of this invention.

DETAILED DESCRIPTION OF THE INVENTION

The process of the present invention is characterized in the steps of causing alpha-amylase to react with starch, thereby forming a saccharified solution consisting mainly of branched dextrin and linear oligosaccharides, and then contacting the resulting saccharified solution with a gel-type filter agent, thereby selectively fractionating the branched dextrin and the linear oligosaccharides in the saccharified solution, respectively.

In the present invention, alpha-amylase is the enzyme reacted with the starch to form a saccharified solution comprising mainly branched dextrin and linear oligosaccharides, while the starch is randomly attacked by the alpha-amylase only at alpha-1,4-linkages of amylose and amylopectin which constitute starch. The resulting saccharified solution contains the so-called branched dextrin containing alpha-1,6-linkages and the linear oligosaccharides containing only alpha-1,4-linkages.

During starch degradation with alpha-amylase, each of the starch components is further reduced in molecular weight and at the limit degradation with alpha-amylase, the saccharified solution contains branched dextrin of a polymerization degree of from 5 to 10. which is referred to as alpha-limit dextrin, linear oligosaccharides mainly of a polymerization degree of from 2 to 6, which contain only alpha-1,4-linkages, and glucose.

In the present invention, corresponding to the required physical properties of the desired products, a saccharified solution of an appropriate degradation stage is contacted with a gel-type filtering agent, e.g., by flowing down from the top of a column filled with the gel-type filtering agent, for instance, an ion exchange resin, and substituting the solution with water in succession. Then, a flow difference is caused between the flow of the branched dextrin and the flow of the linear oligosaccharides in the saccharified solution, and as a result, the branched dextrin is detected in the first effluent fraction and thereafter, the effluent fraction of the linear oligosaccharides is obtained.

In the present invention, in order to prepare a saccharified solution comprising branched dextrin and linear oligosaccharides, the saccharification of starch with alpha-amylase is carried out first.

Various kinds of starches such as corn starch, potato starch, sweet potato starch and tapioca starch which are used as the raw material for producing an ordinary starch sugar as well as alpha-starches thereof and waxy starch may be used as the starting material.

For saccharifying starch, there is a process in which starch is liquefied by a mechanical liquification method accompanied by heating and alpha-amylase is reacted with the thus liquefied starch or a process in which alpha-amylase is added to starch slurry and the mixture is directly heated to promote degradation of the starch, and in compliance with the object, the saccharification of starch may be promoted by the coexistence of beta-amylase.

The extent of starch degradation is generally determined depending upon the required physical properties of the desired product such as viscosity and the degree of sweetness, and also in consideration of the degree of ease of the fractionating treatment carried out thereafter. Under these circumstances, a DE in the range of from 10 to 35 is suitable, DE or Dextrose Equivalent being an indication of total reducing sugars calculated as D-glucose on a dry-weight basis. The DE value is inversely related to the degree of polymerization (DP). Unhydrolyzed starch has a DE of virtually zero, whereas the DE of anhydrous D-glucose is defined as 100.

Although saccharification of starch with alpha-amylase can be carried out at or below the heat-resisting temperature of alpha-amylase, it is possible to carry out the saccharification at a lower temperature after liquefying starch at a high temperature. In consideration of the possible case where the saccharification is promoted in the coexistence of beta-amylase, the temperature range of from 45° to 110° C. is virtually the range of carrying out the process of the present invention. As to pH, a pH is chosen from the range of between about 4.5 and about 7.0 where the enzyme functions.

Although adjusting the control of starch degradation is carried by adjusting the amount of the enzyme added to the reaction system, the operating temperature, the operating time period, etc., the saccharification reaction can be stopped by deactivating the enzyme by heating the system or by adding an acid at the desired end or degradation point during the reaction.

Although the branched dextrin content of the saccharified solution obtained as described above depends of the kind and the degradation degree of the starch, the content is generally in the range of from about 25 to 50% of the solid matter in the system and the rest is the linear oligosaccharides.

It should be understood that pretreatments thought to be useful for the next step of fractionation are included within the scope of the present invention: these pretreatments include usually filtration of the thus obtained saccharified solution for removing the impurities contained in the raw material, purification by decolorizing the system, and concentration of the system.

As the gel-type filtering agent used for fractionation of the branched dextrin and the linear oligosaccharides in the saccharified solution according to the present invention, those usually used materials prepared from dextran, agar-agar, starch, etc. as base materials and ion exchange resins prepared from polystyrene as base material, etc. may be mentioned. Also mixtures of gel-type filtering agents may also be used. Either anion exchange resins or cation exchange resins may be used, however, the cation exchange resins are preferable and particularly the cation exchange resins having a cross-linking degree in the range of from 4 to 8 are practical. Furthermore, concerning the particle diameter of cation exchange resins, to minimize pressure loss in the operation, it is necessary that the particle diameter is in the range of from 40 to 80 mesh and is uniform. Although the cation exchange resins are used as their salt-type, such as Na salt-type, Ca salt-type or Mg salt-type, the Na salt-type is desirable in general.

When the industrial fractionation of branched dextrin and linear oligosaccharides is carried out according to the present invention, the continuous flow of the saccharified solution by a simulated moving bed system comprisingy columns, which have been filled with a gel-type filtering agent and have been connected in multiple stages, is preferred. From 4 to 6 stages are preferably adopted in the simulated moving bed system, and each of the stages is provided with the respective inlets for the original saccharified solution and water and the respective outlets for the branched dextrins and the linear oligosaccharides. A recycle channel is also provided for carrying the transfer of the solution through all the stages.

After flowing the saccharified solution through all the stages, the input and the output of the saccharified solution through each of the stages corresponding to the fractionation pattern is carried out by controlling the flow rate, and in the case where the flow rate of flowing-out is distributed through each of the stages in proportion to the composition ratio of the branched dextrin to the linear oligosaccharides, the saccharified solution can be selectively fractionated into the branched dextrin and the linear oligosaccharides.

Although the concentration of the original saccharified solution treated according to the present invention is economically preferably as high as possible, about 30% to about 50% by weight concentration is practical, in consideration of the pressure loss in the columns. The temperature of the original saccharified solution is preferably maintained at about 50° C. to about 70° C. because the pressure loss in the columns relates also to the temperature of the solution flowing through the columns and temperatures of from about 50° C. to about 70° C. prevent fermentatinn of the saccharified solution. As the water for eluting the products, water which is generally used, distilled water or ion-exchanged water of high purity is used preferably at the same temperature as that at which the solution is flowed.

The branched dextrin fractionated according to the present invention is purified and concentrated by an ordinary method or is spray-dried to give the desired product. The linear oligosaccharides are also treated in the same way as above.

The branched dextrin according to the invention has the following characteristics:

(a) an aqueous 30% by weight branched dextrin solution does not retrodegradate after storing the solution for 30 days at 4° C.,
(b) the mean molecular weight of the branched dextrin is from about 800 to about 16,000 (corresponding DE being from about 20 to about 1), preferably from about 1,000 to about 4,000 (corresponding DE being from about 16 to about 4), and
(c) the viscosity of the branched dextrin is less than about 500 CP.

The branched dextrin product obtained according to the present invention has the following properties:

(1) it does not taste sweet or scarcely tastes sweet,
(2) it dissolves easily in cold water forming a clear solution,
(3) an aqueous solution thereof is not retrograded even at a low temperature without any connection with the concentrations,
(4) it shows a considerably lower viscosity for its DE value than the viscosity of the corresponding ordinary saccharified product,
(5) it makes a clear membrane and the surface of the thus formed membrane is not sticky,
(6) a powdery product thereof is low in hygroscopicity and retains its powdery state even under conditions of high humidity,
(7) it is hardly colored even by heating and has good thermal stability, and
(8) it adsorbs a substance having hydrophobic groups in the presence of water due to the helix structure of the side chains at the terminal of its molecule.

Since the branched dextrin possesses these peculiar properties mentioned as above, it exhibits favorable effects by a single property or by the combination of such properties when utilized in food fabrication. For instance, representative applications include the use of properties (1) and (6), enabling the branched dextrin product to be used as a quantity-increasing agent, extender or diluent for powdery foods, medicines, etc. Further, it can be used as powdery base material for producing powdery soups, powdery spices, etc. by spray-drying while utilizing the properties (2), (3) and (6). Still further, it can be used as viscosity-increasing agent for sauces, dressings, ketchups, etc. by virtue of properties (3) and (4). Furthermore, in the case of mixing the branched dextrin according to the present invention with surimi of fresh fish meat and kneading the mixture, the freezing-denaturation of surimi is prevented and the odor showing a decrease in the freshness of surimi is effectively suppressed by the property (8). In this connections, "surimi" is a wet frozen concentrate of the myofibrillar proteins of fish muscle. Moreover, by utilizing the same property, the branched dextrin according to the present invention improves the whiteness and brightness of the fabricated aquatic products produced by utilizing surimi.

Since the branched dextrin according to the present invention can be supplied as may be required for use as an aqueous solution according to properties (3) and (7) in connection with a particular application, the product is easier and more convenient for the users and is also economical.

The present invention will be explained more concretely while referring to he following non-limitative examples in which all parts and percentages are by weight unless otherwise indicated.

EXAMPLE 1

The separation device used in this example is shown schematically in FIG. 1. There are 4 columns, each identified with a number. A saccharified solution and water, both supplied by a quantitative (metering) pump, supply incoming liquids to each column which are adjusted and fed to the distributor located in the top of each column. Collectors are positioned at the base of each column and valves are provided, one for each column, to the recycle circuit. The recycle circuit is controlled by a quantitative (metering) pump. Branched dextrin is collected in one container, the oligosaccharides are collected in the other.

Corn starch having a moisture content of 13.5% by weight was suspended in water to prepare an aqueous suspension of 20° Be, and after adjusting the pH of the aqueous suspension to 6.2, alpha-amylase (made by NOVO Industry Co., under the trade name of TERMAMIL) was added in an amount of 0.1% by weight of the starch to the aqueous suspension. The thus obtained mixture was subjected to heat treatment for 10 minutes at 105° C. After cooling the thus obtained liquefied starch solution to 65° C., an additional 0.1% by weight of alpha-amylase was added and the mixture was retained at the same temperature for 4 hours to promote saccharification.

The DE value after stopping the reaction by adjusting the pH to 4 using aqueous HCl was 22.7. Then, the thus obtained saccharified solution was subjected to usual decoloration and purification with activated carbon and an ion exchange resin (1:2 ratio by volume mixture of Amberlite IR 120 and Amberlite IRA 411), and the thus decolorized and purified solution was concentrated to a concentration of 40% by weight.

The saccharide composition of the thus obtained saccharified solution consisted of 2% by weight of glucose, 5% by weight of maltose, 15% by weight of maltotriose, 6% by weight of maltotetraose, 12% by weight of maltopentaose, 20% by weight of maltohexaose and 40% by weight of branched dextrin.

Into each column of an apparatus of the simulated moving bed apparatus as shown in the attached FIGURE, which consisted of four columns each with a capacity of 1 liter having a diameter to height ratio of 1:2. each filled with a gel-type polystyrene based, divinylbenzene (DVB) cross-linked, strongly acidic cation exchange resin. The cross-linking degree of the ion exchange resin was 4 and the particle diameter was 60 mesh. The ion exchange resin was used as the Na salt type.

On the upper surface of the internal portion of the columns, distributors were provided and connected respectively to the inlet to the columns for the original saccharified solution and water which had been delivered from quantitative pumps, and the respective outlets from the columns for the fractionated solutions of the branched dextrin and the linear oligosaccharides were connected to the respective collectors provided on the bottom surface of the internal part of the columns. On the outlet and the inlet of each of the columns, electromagnetic valves were provided to control the opening and closing of the valves by a timer, and a recycle channel was provided for transferring the solution through all the stages via a quantitative pump.

The conditions of flowing the solution in the operation of fractionation while using the above-mentioned apparatus were as follows.

The 4 columns were numbered in the direction of the flow of the solution as 1 through 4.

In the first place, 100 ml of the original saccharified solution of a concentration of 40% by weight were passed through column 1 over exactly 10 minutes and 150 ml of water were passed through column 3 over exactly 10 minutes. During that time period, the discharge of the saccharified solution was carried out from the respective columns 2 and 4 while controlling the flow ratio according to the composition ratio of the original saccharified solution, namely the composition ratio (40:60) of the branched dextrin to the linear oligosaccharides. The solution of the branched dextrin was discharged from column 2, and the solution of the linear oligosaccharides was discharged from column 4.

Next, 630 ml (void volume of each column) of the transfer solution was carried out through the recycle channel exactly over 30 minutes and after promoting the fractionation pattern within each column by one step, the out-flow and in-flow of the solution were operated at the position of each column advanced by one step in the same manner as above. The above-mentioned operations were continuously repeated.

During continuous operations, the temperature of the flowing solution and the temperature of water used in the operations were maintained at 60° C. A portion of each of the fractionally collected solutions was respectively purified and then concentrated to be syrup and the remaining part was subjected to spray-drying.

As a result of analysis of the respective specimens, the saccharide composition of the fractionated branched dextrin consisted of 90% by weight of branched dextrin, 3% by weight of maltohexaose, 2% by weight of maltopentaose, 1% by weight of maltotetraose, 2% by weight of maltotriose and 2% by weight of maltose. The DE value of the branched dextrin was 8, corresponding to the mean molecular weight of about 2,000.

The saccharide composition of the linear oligosaccharides consisted of 3% by weight of glucose, 7% by weight of maltose, 25% by weight of maltotriose, 10% by weight of maltotetraose, 20% by weight of maltopentaose, 33% by weight of maltohexaose and 2% by weight of branched dextrin.

EXAMPLE 2

To the saccharified solution of starch obtained in the same manner as in example 1, additional alpha-amylase was added in an amount of 1% by weight based on the starch, and the mixture was subjected to further saccharification for 10 hours at 65° C.

The DE value after carrying out the saccharification showed 34.5 and the saccharide composition of the saccharified solution consisted of 7% by weight of glucose, 12% by weight of maltose, 21% by weight of maltotriose, 8% by weight of maltotetraose, 27% by weight of maltopentaose and 25% by weight of branched dextrin.

Next, the fractionation of the saccharified solution was carried out in the same manner as in example 1. Since the content of the branched dextrin in the original saccharified solution was 25% by weight, except for controlling the discharge ratio 25:75 of the saccharified solution according to the composition ratio (25:75) of the saccharified solution, the same operations as in example 1 were carried out.

The respectively collected fractionated solutions were purified and concentrated to be syrups, and the branched dextrin syrup was spray-dried.

As a result of analysis of the respective specimens, the saccharide composition of the fractionated branched dextrin consisted of 85% by weight of branched dextrin, 10% by weight of maltopentaose, 3% by weight of maltotriose and 2% by weight of maltose. The DE value of the branched dextrin was 16, corresponding to the mean molecular weight of about 1,000.

On the other hand, the saccharide composition of the linear oligosaccharides consisted of 9% by weight of glucose, 15% by weight of maltose, 27% by weight of maltotriose, 11% by weight of maltotetraose, 33% by weight of maltopentaose and 5% by weight of branched dextrin.

EXAMPLE 3

Preparation of a Powdery Soup

Thirty percent (by weight based on the solid matter of a soy sauce) of branched dextrin (DE=12) was added to the soy sauce as a drying adjuvant, and the thus prepared mixture was powdered with a spray-drier at a hot wind temperature of 150° C. after sterilizing the mixture in a plate-type sterilizer.

The moisture content of the thus obtained product was 4% by weight.

Two recipes for powdery soups produced by utilizing the powdered soy sauce are as follows:

Onion Consomme Soup 14.5% by weight of sodium chloride
3.0% by weight of MSG
8.5% by weight of onion essence powder
10.0% by weight of the powdery soy sauce
15.0% by weight of meat essence powder
15.0% by weight of beef essence powder
5.0% by weight of granulated sucrose
0.2% by weight of white pepper
0.1% by weight of celery powder
0.1% by weight of malic acid
3.5% by weight of carrot essence powder, and
25.0% by weight of branched dextrin.

Chicken Cream Soup 6.2% by weight of sodium chloride
2.0% by weight of granulated sucrose
1.0% by weight of MSG
6.0% by weight of the powdery soy sauce
18.0% by weight of powdered cream
10.0% by weight of defatted powdered milk
5.0% by weight of onion essence powder
0.2% by weight of white pepper
0.03% by weight of celery powder
2.0 % by weight of FD chicken powder
1.0% by weight of chicken essence powder
1.2% by weight of locust bean gum
16.0% by weight of potato starch
30.4% by weight of branched dextrin
0.15% by weight of AD parsley, and
0.8% by weight of xanthane gum.

Since powdered soy sauce is hygroscopic, it is desirable to carry out the preparation of powdery foods using the powdered soy sauce in an air-conditioned room with a relative humidity of not higher than 50%. In preparing onion consomme soup, 150 ml of hot water is poured to 6 g of the powdery soup mentioned above. In preparing chicken cream soup, 150 ml of hot water is poured to 13 g of the powdery soup mentioned above.

EXAMPLE 4

Preparation of a Powdery Spice 1 kg of peppermint oil, 1 kg of synthetic menthol and 1 kg of the branched dextrin obtained in example 1 were mixed with 5 liters of water to prepare an emulsion, and the thus obtained emulsion was spray-dried at a drying temperature of from 110° to 120° C. to obtain the product.

EXAMPLE 5

Saccharides, polyphosphoric acid sodium salt and a surfactant were mixed and kneaded according to the following recipe.

|  | Recipe | | |
| --- | --- | --- | --- |
| No. of Recipe | 1 | 2 | 3 |
| Sucrose (wt %) | 3 | 0 | 3 |
| Sorbitol (wt %) | 3 | 3 | 0 |
| Branched dextrin (wt %) (DE = 8) | 0 | 3 | 3 |
| PP Na (wt %) | 0.3 | 0.3 | 0.3 |
| Surfactant available on the market (wt %) | 0 | 0.2 | 0 |

Pollack surimi was mixed with each additive according to the recipes and comparative tests were carried out.

After preserving the surimi added with each of recipes at −20° C., the HW (hunter whiteness), and the L (lightness) of the surimi were measured.

The results are as follows:

| | Just After Refrigeration of Surimi | | | |
| --- | --- | --- | --- | --- |
| No. of specimens | Moisture content (%) | pH | HW (%) | L (%) |
| 1 (Control) | 79.9 | 7.49 | 20.1 | 48.8 |
| 2 | 79.6 | 7.49 | 25.5 | 55.2 |
| 3 | 80.3 | 7.46 | 22.8 | 51.9 |

Pollack surimi mixed with each additive according to the recipes was further mixed with sugar, starch, MSG, etc. and kneaded, and then the mixture was heated at 90° C. for 30 minutes to give kamaboko. The HW, the L and JS (jelly strength) of the kamaboko were measured.

The results are as follows:

| | Physical Properties of the Kamaboko | | | | |
| --- | --- | --- | --- | --- | --- |
| No. of specimens | Moisture content (%) | pH | HW (%) | L (%) | JS (g × cm) |
| 1 (control) | 74.9 | 7.14 | 42.0 | 69.3 | 491 |
| 2 | 74.9 | 7.22 | 44.5 | 71.4 | 491 |
| 3 | 74.9 | 7.24 | 43.2 | 70.5 | 483 |

As are seen in the above test results, branched dextrin added to the food products (surimi and kamaboko) prevented the freeze-deterioration of the food products and at the same time improved the whiteness and the lightness of the food products.

Although the raw surimi subjected to these tests showed some decrease in freshness and gave out a stench, branched dextrin added to such a raw surimi clearly suppressed the stench while exhibiting a deodorizing effect.

What is claimed is:

1. A process for producing branched dextrin which process comprises the steps of:
   (a) reacting alpha-amylase with starch to produce a saccharified solution composed mainly of branched dextrin containing alpha-1,6-linkages and linear oligosaccharides containing alpha-1,4-linkages, and
   (b) contacting the thus obtained saccharified solution with a gel-type filtering agent thereby selectively fractionating and separating said branched dextrin substantially free of said linear oligosaccharices, said branched dextrin having a mean molecular weight of from about 800 to about 16,000.

2. A process according to claim 1, wherein the degree of enzymatic degradation of starch due to alpha-amylase is in the DE range of from 10 to 35.

3. A process according to claim 1, wherein said gel-type filtering agent is an ion exchange resin having a cross-linking degree of from 4 to 8.

4. A process according to claim 1, wherein the selective fractionation of said branched dextrin and said linear oligosaccharides is carried out by a simulated moving bed system.

5. Branched dextrin, substantially free of linear oligosaccharide having a mean molecular weight of from about 800 to about 16,000 with a corresponding DE from about 20 to about 1 produced by the process of claim 1.

6. A solution of branched dextrin, substantially free of linear oligosaccharide, having a mean molecular weight of from about 800 to about 16,000 with a corresponding DE from about 20 to about 1 produced by the process of claim 1.

* * * * *